United States Patent [19]

Schwabe

[11] Patent Number: 5,827,503

[45] Date of Patent: Oct. 27, 1998

[54] METHOD AND COMPOSITION FOR TREATING PERIODONTITIS

[75] Inventor: Christian Schwabe, Charleston, S.C.

[73] Assignee: Collagenex Pharmaceuticals, Inc., Newton, Pa.

[21] Appl. No.: 689,403

[22] Filed: Aug. 8, 1996

[51] Int. Cl.$^6$ ................................. A61K 7/16; A61K 7/22
[52] U.S. Cl. ................................. 424/54; 424/49
[58] Field of Search ........................................ 424/49–58

[56] References Cited

U.S. PATENT DOCUMENTS

| | | | |
|---|---|---|---|
| 2,634,228 | 4/1953 | Kelly et al. | 167/51.5 |
| 3,758,689 | 9/1973 | Rapfogel | 424/329 |
| 4,021,537 | 5/1977 | Saurino | 424/54 |
| 4,036,950 | 7/1977 | Baines et al. | 424/54 |
| 4,110,429 | 8/1978 | Gaffar et al. | 424/54 |
| 4,320,147 | 3/1982 | Schaeufele | 424/329 |
| 4,370,314 | 1/1983 | Gaffar | 424/54 |
| 4,430,323 | 2/1984 | Silver | 424/52 |
| 4,994,262 | 2/1991 | Charbonneau et al. | 424/52 |
| 5,057,497 | 10/1991 | Calam et al. | 514/21 |
| 5,068,107 | 11/1991 | Hollibush et al. | 424/435 |
| 5,145,664 | 9/1992 | Thompson | 424/49 |
| 5,158,763 | 10/1992 | Gaffar et al. | 424/54 |
| 5,160,737 | 11/1992 | Friedman et al. | 424/401 |
| 5,176,901 | 1/1993 | Gallopo et al. | 424/54 |
| 5,178,896 | 1/1993 | Ebine et al. | 424/401 |
| 5,180,575 | 1/1993 | Ha et al. | 404/49 |
| 5,330,746 | 7/1994 | Firedman et al. | 424/49 |
| 5,362,737 | 11/1994 | Vora et al. | 514/291 |
| 5,374,418 | 12/1994 | Oshino et al. | 424/54 |
| 5,438,076 | 8/1995 | Friedman et al. | 514/772.6 |
| 5,496,564 | 3/1996 | Asakura et al. | 424/489 |

FOREIGN PATENT DOCUMENTS

| | | | |
|---|---|---|---|
| 059012 | 1/1982 | European Pat. Off. | A61K 7/22 |
| 1525254 | 9/1978 | United Kingdom | A61K 7/16 |
| PCT/WO 95/20971 | 8/1995 | WIPO | A61K 33/42 |

OTHER PUBLICATIONS

E. Feldbau and C. Schwabe, Selective Inhibition of Serine Protease by Alkyldimethylbenzyl–ammonium Chloride, Biochemistry: 10, 2131–2138 (1971).

M. Addy, et al., The Effect of Some Chlorhexidine–Containing Mouthrinses On Salivary Bacterial Counts, J. Clin. Periodonotol. 18:90–93 (1991).

K. Baker, Mouthrinses in the Prevention and Treatment of Periodontal Disease, Current Opinion in Periodontology 1993:89–96 (1993).

A. Elworthy et al., The Substantivity of a Number of Oral Hygiene Products Determined by the Duration of Effects on Salivary Bacteria, J. Periodontol. 67:572–576 (Jun. 1996).

*Primary Examiner*—Shep K. Rose
*Attorney, Agent, or Firm*—Hoffmann & Baron, LLP

[57] ABSTRACT

Oral hygiene is improved and diseases of the oral cavity are treated by oral application of a composition containing 0.02 to 0.25 weight percent alkyldimethylbenzylammonium chloride (BAC) and 0.05 to 2.0 weight percent sodium chloride dissolved in water, in the absence of other active ingredients. The BAC and sodium chloride act synergistically to allow the composition to sorb strongly to oral tissues and remain there for several hours.

20 Claims, No Drawings

METHOD AND COMPOSITION FOR TREATING PERIODONTITIS

This invention relates to a method and composition for oral hygiene and for the non-invasive treatment of diseases of the oral cavity, including periodontitis and related forms of gingival disease, by oral application of a solution containing alkyldimethylbenzylammonium chloride and sodium chloride as the sole active ingredients.

BACKGROUND OF THE INVENTION

Diseases of the oral cavity include periodontitis, gingivitis, dental caries, halitosis, aphthous ulcers and plaque formation. Microorganisms are implicated in many diseases of the oral cavity. For example, periodontal diseases, including periodontitis and gingivitis, are caused by bacteria that form plaques on the surfaces of the teeth at the gingival sulcus or pocket. Current methods of treatment of periodontal diseases depend on the severity of the disease. Mild cases are generally treated by the removal of mechanical irritants such as calculus. More severe cases are treated surgically by removal of gingival tissue, polishing of tooth roots, or occasionally by splinting of the teeth. Surgical intervention is a painful and costly procedure.

Prophylactic measures can be taken to forestall the occurrence, or reoccurrence of periodontal disease. Known prophylactic measures include regular removal of calculus and plaque and the use of dental floss. Such measures are generally time consuming and involve a strict regimen of care to be effective. For this reason, known prophylactic measures are rarely completely effective in preventing diseases such as periodontal disease.

Very few, if any, antibacterial agents have been effectively used alone for oral disinfection. Chlorhexidine and cetylpyridinium chloride have been separately tested for this purpose. A. Elworthy, et al., "The Substantivity of a Number of Oral Hygiene Products Determined by the Duration of Effects on Salivary Bacteria", J. Periodontol. 67:572–576 (1996). A. Elworthy et al., determined that efficacy for persistence of action of antimicrobial agents in the mouth cannot be assumed merely because a product contains a known active agent (J. Periodontol. vol. 67 at page 572). M. Addy et al., "The Effect of Some Chlorhexidine-Containing Mouthrinses On Salivary Bacterial Counts", J. Clin. Periodontol. 18:90–93 (1991) also studied the oral effects of chlorhexidine. Baker, K., "Mouthrinses In the Prevention and Treatment of Periodontal Disease", Current Opinion In Periodontology pp 89–96 (1993) reviewed the use of chlorhexidine, stannous fluoride, phenolic compounds, cetylpyridinium chloride and triclosan for oral rinses. Benzalkonium chloride was not suggested in these articles.

Many and varied mouthwash formulations are described in the patent literature for use in oral hygiene. These formulations generally include one or more active ingredients, usually in extensive and expensive formulations. Some of these formulations utilize quaternary ammonium compounds or benzalkonium chloride as a preservative or germicide among numerous other ingredients. Illustrative of these are U.S. Pat. Nos. 4,110,429, 5,145,664, 5,362,737 and 5,374,418. There is no suggestion to limit the active ingredients to benzalkonium chloride and sodium chloride.

U.S. Pat. No. 3,758,689 describes jet stream application of a dilute aqueous solution of 0.005 to 0.1 percent by weight of benzalkonium chloride for penetration into periodontal pockets. Because the concentration of benzalkonium chloride is on the whole very low, it appears that the mechanical effect of the jet stream manner of application is critical.

It is an object of the invention to provide a composition and method for oral hygiene and for the treatment and prevention of oral diseases, simply, inexpensively and yet highly effectively as compared with previously known formulations and methods.

It is a further object of the invention to provide a composition which persists in the mouth for a sustained period of time, for example, at least overnight.

SUMMARY OF THE INVENTION

Oral hygiene is promoted and diseases of the oral cavity, including dental caries, gingivitis, halitosis, aphthous ulcers, plaque formation, and periodontal disease are effectively treated by the oral application of a composition containing alkyldimethylbenzylammonium chloride and sodium chloride dissolved in water. The two ingredients interact to increase substantivity and no other active ingredients are required in the composition for superior results. By active is meant having an anti-oral disease or anti-periodontal disease therapeutic effect. Substantivity is the persistence of action. The composition is applied orally in an amount effective to promote oral hygiene, to reduce or prevent periodontal disease, or to alleviate diseases of the oral cavity.

Treatment includes orally rinsing with a composition containing a preferred range of from about 0.02 to about 0.25 weight percent alkyldimethylbenzylammonium chloride and a preferred range of about 0.05 to about 2.0 weight percent sodium chloride in water.

In a more preferred range, the amount of alkyldimethylbenzylammonium chloride is above 0.1 weight percent to about 0.2 weight percent. A more preferred range of sodium chloride is from about 0.05 weight percent to about 1.5 weight percent.

Advantageously, the composition has a tendency to adsorb strongly onto the oral tissues and remain there for a period of at least several hours resulting in sustained substantivity or persistence of action. The adsorption is enhanced by the sodium chloride in the composition. The adsorption factor helps to maintain an essentially germ free oral cavity for several hours, through the night, or until food is consumed. Even after several hours and when food is consumed, a residual protection remains so that maintenance application can be interrupted by a few days.

DETAILED DESCRIPTION OF THE INVENTION

A number of oral diseases are caused by microorganisms. For example, periodontal disease involves inflammation of gingival tissues in response to the actions of oral bacteria. The gingiva appear red and swollen, and have a tendency to bleed when the teeth are brushed. As the disease progresses, the attachment between the gums and the tooth may be broken. This creates a space, or periodontal pocket, between the tooth and gum which can serve as a center for enhanced microbial growth. Such growth can lead to the formation of abscesses and bone loss in the alveolar crest. The consequence of advanced periodontal disease is a loosening of the teeth and ultimately tooth loss.

Periodontitis can affect a broad population from prepubertal to adult, generally increasing in prevalence and severity with increasing age. Periodontitis may also be a secondary problem in persons with other diseases such as patients receiving cancer chemotherapy or those afflicted with arthritis.

Dental caries is a disease of calcified tissues of the teeth resulting from the action of microorganisms on carbohydrates, characterized by decalcification of the inorganic portions of the tooth and accompanied by or followed by disintegration of the organic portion. Halitosis is offensive breath. Aphthous ulcers are spots in the mouth that characterize aphthous stomatitis. Aphthous stomatitis can be associated with infection by a pleomorphic transitional L-form of a α-hemolytic streptococcus. Dental plaque is characterized by a mass adhering to the enamel surface of a tooth, composed of a mixed colony of bacteria in an intracellular matrix of bacterial and salivary polymers and remnants of epithelial cells and leukocytes.

It has now been found that the alkyldimethylbenzylammonium chloride (benzalkonium chloride or BAC) in the composition of the invention is more effective than chlorhexidine for oral disinfection. Moreover, the composition of the invention adsorbs onto gingival and tooth surfaces for prolonged germicidal activity, whereas chlorhexidine must be used twice daily for the same effect. Other well-known antibacterials, such as benzethonium chloride and cetylpyridonium chloride have only limited effectiveness in prophylaxis.

The composition effectively reverses and prevents periodontal disease through the action of alkyldimethylbenzylammonium chloride (BAC). Furthermore, although the BAC solution is effective by itself, the presence of sodium chloride amplifies the adherence of the BAC to gingival and tooth surfaces. Indeed, the combination of BAC and sodium chloride persists longer in the treated area than either of the two components separately thus showing synergy. The dissociation of the BAC from the surface is very slow as demonstrated by the persistence of a slight bitterness and the lack of mal odor. The bitter taste can be removed by tooth-brushing.

BAC suitable for use in the invention is a mixture of alkyldimethylbenzylammonium chlorides of the general formula

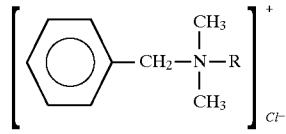

in which R represents a mixture of alkyls from $C_8H_{17}$ to $C_{18}H_{37}$. The Merck Index, S. Budavari, ed., Merck & Co., Inc. 1989, entry 1066 at page 165.

In the invention, the BAC used is an equimolar mixture of alkyldimethylbenzylammonium chlorides having a straight chain alkyl substituent of from 12 to 18 carbons. BAC is commercially available as a compound for use in cold sterilization of surgical instruments. Some of these commercially available BAC's are Benirol, Capitol, Cequartyl, Drapolene, Germinol and Zephiran Chloride.

The BAC solution in water can be used alone, but its adherence to oral tissues for prolonged activity is enhanced by sodium chloride preferably at physiological levels. The sodium chloride causes the BAC to adhere more tightly to the treated tissues.

The BAC and sodium chloride are dissolved in water to form a mouthwash, which can be formulated as a gel as well as a liquid. For simplicity and economy, a liquid is preferred.

A solution of the components is prepared in water in amount to result in 100 weight percent total composition. The pH of the composition is preferably compatible with oral tissues. The composition can optionally include non-active additives to enhance the appearance or taste of the composition, for example, alcohol up to about 2 weight percent, and coloring and/or, flavoring agents as are known in the art. Non-limiting examples of flavoring agents include the mint-flavorings such as oil of spearmint, oil of peppermint and oil of wintergreen, and other oils including citrus, clove, eucalyptus, etc. Colorants may be chosen from those approved by the FDA, such as Blue Nos. 1 and 2, Green No. 6, Red Nos. 3 and 40, and Yellow Nos. 5 and 6. Non-fermentable sugars or sugar substitutes may also be added where a sweetened vehicle is desired. These include sugar alcohols, sorbitol, xylitol, maltitol, saccharines, aspartame, sucaryl or the like. Flavorants and sweeteners are used in small amounts, e.g., up to about 0.25 weight percent, preferably up to about 0.05 weight percent.

Known anti-stain additives e.g., in an amount of about 0.01 to 0.1 weight percent, may also be added, such as phosphorous-containing and organo-phosphorous-containing compounds. But for staining which may occur, it is preferred to utilize the composition of the invention both as a mouthrinse and incorporated into a toothpaste, for example as a gel component. In a preferred treatment method to avoid staining, both a mouthrinse and a tooth-brushing with the composition of the invention are undertaken in the morning, while in the evening, the mouthrinse alone is used. However, the composition can always be used in mouthwash form alone.

Additives which adversely interact with BAC should be avoided, for example, surfactants, particularly anionic surfactants.

A mouthwash according to this invention is used regularly to treat diseases of the oral cavity, including as non-limiting examples, periodontitis, gingivitis, dental caries, halitosis, aphthous ulcers and plaque formation.

A mouthwash according to this invention is preferably used regularly to treat periodontal disease, preferably until redness and swelling of the gums are alleviated. Preferably, the mouthwash is applied daily, following the last food of the day. Reduction of gingival inflammation generally results within two days of the inception of treatment, and in some cases may be effected with only a single application. The composition can be applied to the gums and teeth by simply swishing the mouthwash around in the oral cavity. Preferably, contact with the mouthwash is maintained for from 5 to 15 seconds. The mouthwash may also be advantageously gently introduced into the lumen of a periodontal pocket or abscess using a blunt-needled syringe. The composition can also be advantageously used pre- and post-operatively for oral surgery and during orthodontic treatment. The composition can also be used as a diagnostic tool. If a patient does not respond after proper use within 2–4 days, other causation such as allergies and blood dyscrasias should be explored.

For use, the composition may be applied either in a mouthwash or in a toothpaste. A toothpaste according to this invention contains BAC and sodium chloride in an otherwise conventional toothpaste formulation containing components which do not interfere with the composition, e.g., a dentifrice preferably containing abrasives such as insoluble organic salts, thickening agents (carboxymethylcellulose, carrageenan), flavorings, foaming agent, humectant (glycerol, sorbitol), and water. Standard abrasives include dicalcium phosphate, insoluble sodium metaphosphate, calcium pyrophosphate, calcium or magnesium carbonate, hydrated aluminum oxide, silicates and dehydrated silica gels. Such a toothpaste used regularly will effectively prevent the onset of periodontal disease.

While it is not intended to be bound by theory, it is believed that the BAC component acts at least in part, as a serine protease inhibitor on the tissues of the oral cavity. At the same time, the sodium chloride aids the substantivity, helping the composition to persist in the mouth. Our evidence suggests that interaction of the enzyme and BAC includes the protonation of a carboxyl group permitting BAC to slip into the hydrophobic pocket of the enzyme which contains the active site. E. Feldbau and C. Schwabe, "Selective Inhibition of Serine Proteases by Alkyldimethylbenzyl-Ammonium Chloride", Biochemistry 10:2131–2138 (1971). Mammalian and bacterial serine proteases are believed to have similar active site environments. Moreover, it is believed that the bacterial infection which is the causative agent in periodontitis elicits an inflammatory host response in the tissues of the periodontium, causing the release of a variety of cytokines and other inflammatory mediators. These mediators cause a pathological elevation in tissue degradative enzymes, of which serine proteases such as neutrophil elastase and matrix metalloproteinases (MMPs) such as neutrophil collagenase are examples. It has been shown that administration of MMP inhibitors such as doxycycline can slow the progression of the chronic tissue destruction which characterizes chronic adult periodontitis, presumably through inhibition of pathologically elevated MMP activity. It is postulated that the administration of serine protease inhibitors such as the BAC compounds could also contribute to a reduction in the rate of tissue destruction during chronic periodontitis due to inhibition of pathologically elevated serine protease activity.

The following non-limiting examples will serve to illustrate the use and effectiveness of compositions according to this invention.

The composition of the invention was prepared by dissolving BAC in various concentrations in water. The composition will be termed "Composition G."

Test microorganisms

The following three test microorganisms were obtained from the American Type Culture Collection one month prior to the initiation of the study.

Streptococcus mutans ATCC 25175

Actinomyces viscosus ATCC 19246

Candida albicans ATCC 18804

Each lyophilized culture was plated onto Trypticase-soy agar supplemented with 5% whole defibrinated sheep blood (TSBA) and incubated at 37° C. until growth was apparent.

S. mutans and A. viscocus were incubated in an anaerobic chamber with an atmosphere of 10% $H_2$, 10% $CO_2$, and 80% $N_2$; C. albicans was incubated aerobically. Each strain was transferred after visible growth was present to fresh TSBA for colony separation and validation of purity. These plates were visibly inspected for purity after 48 h of incubation and transferred to Brain Heart Infusion (BHI) agar (BBL #11065). The cultures were maintained on BHI agar with weekly transfer for the duration of the study.

Prior to use, each microorganism was cultivated in BHI broth (BBL #11059) as follows:

| Test microorganism | Culture age | Incubation conditions |
|---|---|---|
| Streptococcus mutans ATCC 25175 | 16–18 h | anaerobic @ 37° C. |
| Actinomyces viscosus ATCC 19246 | 32–36 h | anaerobic @ 37° C. |
| Candida albicans ATCC 18804 | 32–36 h | aerobic @ 37° C. |

EXAMPLE 1

Bactericidal effect

The bactericidal effect of Composition G at 0.02, 0.12, 0.17, and 0.22% was tested against each test microorganism. Peridex® (Proctor and Gamble) containing 0.12% chlorhexidine gluconate and Cool Mint Listerine® (Warner Lambert) were used as positive controls and water was used as a negative control. Listerine is the trademark for an antiseptic solution containing boric acid, benzoic acid, thymol, and essential oils of Eucalyptus, Gaultheria, etc. Cool Mint Listerine contains as listed active ingredients 0.064% thymol, 0.092% Eucalyptol, 0.060% methyl salicylate and 0.042% menthol. Other ingredients are water, sorbitol solution, 21.6% alcohol, Poloxamer 407, benzoic acid, flavoring, sodium saccharine, sodium citrate, citric acid and coloring. A culture of the test microorcanism was mixed with an equal volume of serum, added to the test antiseptic, and incubated for 10 min at 37° C. A series of dilutions were made and plated using BHI broth and agar without the incorporation of any neutralizers. The results of two separate trials are given in Table 1.

TABLE 1

Bactericidal effect of oral antiseptic agents on the test microorganisms, S. mutans, A. viscosus, and C. albicans

| | S. mutans 25175 | | A. viscosus 19246 | | C. albicans 18804 | |
|---|---|---|---|---|---|---|
| Antiseptic | Ave CFU | Rel %* | Ave CFU | Rel % | Ave CFU | Rel % |
| Peridex ® 0.12% chlorhexidine | No growth** | NA | No growth | NA | No growth | NA |
| Cool Mint Listerine ® | No growth | NA | $8.5 \times 10^5$ | 2.9 | No growth | NA |
| 0.02% Composition G | No growth | NA | $5.5 \times 10^6$ | 19.0 | No growth | NA |
| 0.12% Composition G | No growth | NA | No growth | NA | No growth | NA |
| 0.17% Composition G | No growth | NA | No growth | NA | No growth | NA |
| 0.22% Composition G | No growth | NA | No growth | NA | No growth | NA |
| Water control | $5.7 \times 10^8$ | 100 | $2.9 \times 10^8$ | 100 | $6.7 \times 10^8$ | 100 |

*Percent of CFUs relative to water control CFU = colony forming unit
**No visible growth on any dilution plates ($10^{-1}$ to $10^{-5}$)

All antiseptic products gave an apparent 100% kill within 10 min of incubation of the test organism with the antiseptic with the exception of Cool Mint Listerine and 0.02% Composition G against *A. viscosus*. Cool Mint Listerine gave approximately a 97% kill (2.5 $\log_{10}$ reduction) for *A. viscosus*. Peridex, containing 0.12% chlorhexidine gluconate, and Composition G, at 0.12% and above, resulted in 8 $\log_{10}$ reduction for all three test microorganisms since no CFUs were detected for any of the test organisms at the lower dilution plated ($10^{-1}$).

EXAMPLE 2

Bacteriostatic effect

The bacteriostatic effect of the four concentrations of Composition G was tested. Peridex and Cool Mint Listerine were used as positive controls with water as a negative control. Each microorganism in 50% serum was added to the test antiseptic and incubated for 10 min at 37° C. Aliquots of 1.0 ml were used to inoculate 100 ml BHI broth cultures. The broth cultures were incubated 48 h and then a series of serial dilutions were plated to BHI agar. No neutralizers were added to either the BHI broth or agar. The results are given below in Table 2.

All four Composition G concentrations resulted in the total inhibition of the three test organisms since no growth was detected in any of the agar plates after 48 h of incubation. These included plates which had been seeded with a 1.0 ml aliquot directly from the 100 ml broth culture. The chlorhexidine positive control resulted in the complete inhibition of *C. albicans*, a 7–8 $\log_{10}$ inhibition of *S. mutans*, and a 3 $\log_{10}$ inhibition of *A. viscosus* relative to the water control. The Listerine positive control resulted in a 0.5–1 $\log_{10}$ inhibition of the test microorganisms.

organism relative to the cell counts obtained with the water control. The bacteriostatic effects of Composition G at 0.02% were superior to both Peridex and Cool Mint Listerine based on the reductions obtained in cell counts.

In conclusion, the in vitro effects obtained with Composition G concentrations of 0.12% and above were superior to those obtained with 0.12% chlorhexidine. The 0.02% concentration of Composition G produced a bacteriostatic effect equivalent or superior to 0.12% chlorhexidine with all three test organisms. The bactericidal effect of 0.02% Composition G was equivalent to that obtained with 0.12% chlorhexidine for both *S. mutans* and *C. albicans* but was less effective against *A. viscosus*.

Composition G concentrations of 0.12, 0.17, and 0.22% produced a 3 $\log_{10}$ reduction in the number of viable cells per ml for each of the test microorganisms regardless of whether the results are based on bactericidal or bacteriostatic effects.

Surprisingly, the 0.02% Composition G was also effective against all of the test organisms, with a lower bactericidal effect against *A. viscosus*.

Based on the data obtained, a Composition G concentration greater than 0.02% but less than 0.12% yields reductions in the test microorganisms equivalent to 0.12% chlorhexidine.

IN VIVO TESTING

Patients were treated for periodontal disease using the composition of the invention.

In the following examples, patient treatment phase included application of the composition of the invention in

TABLE 2

Bacteriostatic effect of oral antiseptic agents on the test microorganisms

| Antiseptic | *S. mutans* 25175 | | *A. viscosus* 19246 | | *C. albicans* 18804 | |
|---|---|---|---|---|---|---|
| | Ave CFU | Rel %* | Ave CFU | Rel % | Ave CFU | Rel % |
| Peridex ® 0.12% chlorhexidine | $3.0 \times 10^1$ | <0.001 | $1.8 \times 10^4$ | 0.02 | No growth** | NA |
| Cool Mint Listerine ® | $3.8 \times 10^7$ | 25.3 | $3.2 \times 10^6$ | 4.2 | $3.8 \times 10^8$ | 58.5 |
| 0.02% Composition G | No growth | NA | No growth | NA | No growth | NA |
| 0.12% Composition G | No growth | NA | No growth | NA | No growth | NA |
| 0.17% Composition G | No growth | NA | No growth | NA | No growth | NA |
| 0.22% Composition G | No growth | NA | No growth | NA | No growth | NA |
| Water control | $1.5 \times 10^8$ | 100 | $7.7 \times 10^7$ | 100 | $6.5 \times 10^8$ | 100 |

*Percent of CFUs relative to water control
**No visible growth from 1.0 ml aliquots plated directly from 100 ml batch culture or on any of the dilution plates ($10^{-1}$ to $10^{-5}$)

Discussion of bactericidal and bacteriostatic effects:

Composition G at a concentration of 0.12% and above resulted in an 8 $\log_{10}$ reduction in all three test microorganism relative to the water control. The lowest Composition G concentration tested, 0.02%, was effective against both *S. mutans* and *C. albicans* and a 2 $\log_{10}$ reduction for *A. viscosus*. The bactericidal effect of 0.02% Composition G was roughly equivalent to the effect obtained with Cool Mint Listerine while the bactericidal effect of 0.12% Composition G and above was superior to 0.12% chlorhexidine gluconate.

The bacteriostatic effects obtained with all four concentrations of Composition G were striking. Composition G, at the lowest concentration of 0.02%, resulted in the total inhibition of the test microorganisms. This was equivalent to an 8 $\log_{10}$ reduction in the cell numbers for each test the form of a mouth rinse once at night, after the last intake of food or drink and after normal tooth brushing. A daily schedule of this regimen was recommended for treatment of periodontal disease. For maintenance and prophylaxis, the rinse is recommended every second or third day under the same circumstances.

Improvement was gauged subjectively by the patient and objectively by the obviation of surgical intervention as determined by the health care provider.

EXAMPLE 3

A 38-year old male was referred for periodontal surgery (gingivectomy) to eliminate deep pockets in the molar region, general fragility of gingiva due to local inflammation and associated tooth mobility (Grade 1). At this stage, a treatment phase according to the invention was initiated. Within three days, all visible inflammation and bleeding had ceased. The pockets remained asymptomatic and after one year follow-up, tooth mobility could no longer be detected. Surgery was not performed.

EXAMPLE 4

A 52-year old female was diagnosed as having moderate gingivitis with substantial pocket formation and periodontal inflammation in the upper and lower molar region, and surgery was scheduled. A treatment phase according to the invention was instituted. After one week of treatment, the conditions had improved to the extent that surgery became unnecessary.

EXAMPLE 5

A 45-year old female complained of inflamed gingiva, tooth mobility and a receding dentogingival junction. In addition, she was a heavy smoker. A treatment phase was instituted and maintenance was followed for three years. Substantial and persistent improvement was confirmed on dental examination.

EXAMPLE 6

A woman in her seventies was slated for periodontal surgery. A treatment phase was initiated and thereafter maintenance was followed. Surgery became unnecessary. Even after three years, surgery was still no longer indicated.

Compositions according to this invention give excellent results when used in the treatment and prevention of periodontal disease. It will be understood, however, that in very advanced cases of periodontal disease surgical intervention may still be necessary. In these circumstances, compositions containing BAC and sodium chloride are advantageously used to reduce (gingival inflammation prior to surgery and as a prophylactic regimen following surgery.

While there have been described what are presently believed to be the preferred embodiments of the invention, those skilled in the art will realize that changes and modifications may be made thereto without departing form the spirit of the invention and it is intended to claim all such changes and modifications as fall within the true scope of the invention.

I claim:

1. A method for improving oral hygiene comprises oral application of a composition consisting essentially of alkyldimethylbenzylammonium chloride, sodium chloride and water, said composition applied in an amount to improve oral hygiene.

2. A method for treating diseases of the oral cavity comprises oral application of a composition consisting essentially of alkyldimethylbenzylammonium chloride, sodium chloride and water, said composition applied in an amount to alleviate or prevent diseases of the oral cavity.

3. The method of claim 2 wherein the disease is periodontitis, gingivitis, halitosis, aphthous ulcer or plaque formation.

4. The method of claim 2 wherein the composition further comprises at least one member of the group consisting of alcohol, flavorants, colorants and anti-stain compounds.

5. The method of claim 2, wherein the alkyldimethylbenzylammonium chloride has an alkyl group having from 12 to 18 carbons in a straight chain.

6. The method of claim 2, wherein the alkyldimethylbenzylammonium chloride is in an amount of from about 0.02 to about 0.25 weight percent and the sodium chloride is in an amount from about 0.05 weight percent to about 2.0 weight percent.

7. The method of claim 2, wherein the alkyldimethylbenzylammonium chloride is in an amount of above about 0.1 to about 0.2 weight percent and the sodium chloride is in an amount of about 0.05 to about 1.5 weight percent.

8. The method of claim 2 wherein the disease is gingivitis.

9. The method of claim 2 wherein the disease is halitosis.

10. The method of claim 2 wherein the disease is aphthous ulcer.

11. The method of claim 2 wherein the disease is plaque formation.

12. The method of claim 2 wherein the disease is periodontal disease.

13. A composition for oral application consisting essentially of about 0.02 to about 0.25 weight percent alkyldimethylbenzylammonium chloride, about 0.05 weight percent to about 2.0 weight percent sodium chloride and water.

14. The composition of claim 13, further comprising up to 2% alcohol.

15. The composition of claim 13, further comprising flavorants, colorants, or anti-stain compounds, respectively in flavoring, coloring or anti-staining amounts.

16. The composition of claim 13, wherein the alkyldimethylbenzylammonium chloride has an alkyl group having from 12 to 18 carbons in a straight chain.

17. The composition of claim 13, wherein the alkyldimethylbenzylammonium chloride is in an amount of above 0.1 to about 0.2 weight percent and the sodium chloride is in an amount of about 0.05 to about 1.5 weight percent.

18. The method of claim 1 wherein the oral application is by oral rinsing.

19. The method of claim 2 wherein the oral application is by oral rinsing.

20. The composition of claim 13 wherein the composition is in the form of a mouthwash or toothpaste.

* * * * *